United States Patent [19]
Lim et al.

[11] Patent Number: 5,552,312
[45] Date of Patent: Sep. 3, 1996

[54] RECOMBINANT $HT_{M4}$ GENE, PROTEIN AND ASSAYS

[75] Inventors: Bing Lim, Dorcester; Chaker N. Adra, Boston, both of Mass.; Jean-Michel Lelias, Toulouse, France

[73] Assignee: Beth Israel Hospital Boston, Boston, Mass.

[21] Appl. No.: 318,492

[22] Filed: Oct. 6, 1994

[51] Int. Cl.$^6$ .............................. C12N 5/00; C12N 1/20; C12N 15/00; C07H 21/04
[52] U.S. Cl. .................................. 435/240.2; 435/252.3; 435/320.1; 536/23.5
[58] Field of Search ............................. 435/69.1, 240.2, 435/320.1; 530/350; 536/23.5

[56] References Cited

PUBLICATIONS

Shirakawa, Taro et al., "Association between atopy and variants of the β subunit of the high–affinity immunoglobulin E receptor," *Nature Genetics* 7:125–130 (1994).
Ravetch, Jeffrey V., "Atopy and Fc receptors: mutation is the message?", *Nature Genetics* 7:117–118 (1994).
Kobayashi, Hirofumi et al., "Variability of 11q23 Rearrangements in Hematopoietic Cell Line Identified With fluorescence In Situ Hybridization," *Blood* 81(11):3027–3033 (1993).
Ravetch, Jeffrey V. and Kinet, Jean–Pierre "Fc Receptors," *Annu. Rev. Immunol.* 9:457–492 (1991).
Cookson, W. O. C. M. et al., "Maternal inheritance of atopic IgE responsiveness on chromosome 11q," *The Lancet* 340:381–384 (1992).
Cookson, William O. C. M. et al., "Linkage between Immunoglobuline Responses Underlying Asthma and Rhinitis and Chromosome 11q," *The Lancet:* 1292–1295, Jun. 10, 1989.
Davies, Kevin "Allergy by mutation," *Nature* 369:506 (1994).
Marsh, David G. and Meyers, Deborah A. "A major gene for allergy—fact or fancy?", *Nature Genetics* 2:252–254 (1992).
Adra, et al. (1994) Proc. Natl. Acad. Sci. USA 91: 10178–10182.
Kinet, et al. (1988) Proc. Natl. Acad. Sci. USA 85: 6483–6487.
Kuster, et al. (1992) J. Biol. Chem. 267: 12782–12787.
Maekawa, et al. (1992) FEBS lett. 302: 161–165.
Ra, et al. (1989) J. Biol. Chem. 264: 15323–15327.

*Primary Examiner*—Robert A. Wax
*Assistant Examiner*—Lisa J. Hobbs
*Attorney, Agent, or Firm*—Hamilton, Brook, Smith & Reynolds, P.C.

[57] ABSTRACT

The invention relates to a recombinant DNA molecule which encodes a $HT_{m4}$ protein, a transformed host cell which has been stably transfected with a DNA molecule which encodes a $HT_{m4}$ protein and a recombinant $HT_{m4}$ protein. The invention also relates to a method for detecting the presence of a hereditary atopy.

6 Claims, 2 Drawing Sheets

```
  1  GTG ATC TTT TCT GAG TGT CTC CTA CTT GCG ACA AGG TGG ACT TGG GAG GAA AGC CGT CTG
 61  CCA AAG CCT GAA GCC TCC AAG CCA TAA ACA ACC CCA ATG GCC TCC CAC GAA GTT GAT AAT    8
     met ala ser his glu val asp asn 121  GCA GAG CTG GGG TCA GCC TCT GCC CAT GGT GCC CAT GGT ACC CCA GGC AGT GAG GGA CCA GAA GAG   28
     ala glu leu gly ser ala his gly thr pro gly ser glu pro glu 181  CTG AAT ACT TCT GTC TAC CAC CCC ATA AAT GGA TCA CCA GAT TAT CAG AAA GCA AAA TTA   48
     leu asn thr ser val tyr his pro ile asn gly ser pro asp tyr gln lys ala lys leu 241  CAA GTT CTT GGG GCC ATC CAG AAT GCA GCA ATG AAT CTG GCT TTG GGT GTC TTT   68
     gln val leu gly ala ile gln asn ala ala met ile leu ala leu gly val phe 301  CTG GGT TCC TTG CAA TAC CCA TAC CAC TTC CAA AAG CAC TTC TTT TTC TTC TAC   88
     leu gly ser leu gln tyr pro tyr his phe gln lys his phe phe phe phe tyr 361  ACA GGC TAC CCG ATT TGG GGT GCT GTG TTT TTC TGT AGT TCA GGA ACC TTG TCT GTA  108
     thr gly tyr pro ile trp gly ala val phe phe cys ser ser gly thr leu ser val val 421  GCA GGG ATA AAA CCC ACA AGA ACA TGG ATA CAG AAV AGT TTT GGA ATG AAC ATT GCC AGT  128
     ala gly ile lys pro thr arg thr trp ile gln asn ser phe gly met asn ile ala ser 481  GCT ACA ATT GCA CTA GTG GGG ACT GCT TTT CTC TCA CTA AAT ATA GCA GTT AAT ATC CAG  148
     ala thr ile ala leu val gly thr gly thr ala phe leu ser leu asn ile ala val asn ile gln 541  TCA TTA AGG AGT TGT CAC TCT TCA TCA GAG TCA CCG GAC CTA TGC AAT TAC ATG GGC TCC  168
     ser leu arg ser cys his ser ser ser glu ser pro asp leu cys asn tyr met gly ser 601  ATA TCA AAT GGC GTG ATG GTG TCT CTA CTG CTG CTT CTC ACC TTG CTG GAA TTA TGC GTA ACT  188
     ile ser asn gly met val ser leu leu leu leu thr leu leu glu leu cys val thr 661  ATC TCT ACC ATA GCC ATG TGG TGC AAT GCA AAC TGC TGT AAT TCA AGA GAG GAA ATT TCC  208
     ile ser thr ile ala met trp cys asn ala asn cys cys asn ser arg glu glu ile ser
```

FIGURE 1A

```
                                                                                214
721  TCA CCT CCC AAT TCT GTG TAA TCA AGA ATA CCT TAT GAA AAT AAT TCT GAG AGC ATG
     ser pro pro asn ser val END 781  AAT ATT TGA CCT TAA ATC TCC AGT GAC TCA GAG CTT CAC CCA CAA ACT CAG GAG AAC ATA
841  AGC CTG CTC GTA AAG CTC TCT CCT TCT ATC ATG GCA CCA ATC ACA AGA ACC TTG GAC GTT
901  TGA CTG ACT CTA TCC CTC TAA TAA CTA TTT GTG ATC TTT AAC TAT
961  AGG ACA GAT ATA TTT CTT GCA TTC GAT ATC TGT ACC TGT TAC TCC
1021 AAA GTT GTT TCC AGA AAT TGG AAT TTC TAT TTA TCC TTT ATT TCT AAA ATT GCT TTA TGA
1081 GGT TTA AGG AAG GAA GGC GGT ATA ATC CCT ATT CAA TTT AAA GAG AAA ATC CAA CTT
1141 CTG ACC GCC CAG TAG GAA TGA AAA AAA TGA TTT ACA TCC ATT TCT TGC TTC TTG
1201 ACT TTA ACA TCA GCA TTA AAA GTG TCA AAA TTA CCA AAT TTA TCA TTA AAA
1261 TAA ATT TTC ACT GTA TTT GAG GGG CTC AGG GAT TTT ATT TCA GTG GAG
1321 TGC TGG AAC TCA CAC. ATG CCC TGA TAT GTA AAT GGA TTA TGT TGG CGA GAA CTA AAG AAT
1381 CAA GCC CAA ATG TCT TCA CAC ATC TGG GTT CAA ATT CTG TTT TTC ATT ACC TGT
1441 AAG GCC TTT AGA ATC TGA CTC AAT CTC GAT CTA TTT CTC TGT TAA ATA GGT
1501 ATG AAC ATG GGC AAA ACT TTA TCT AAT TCG AGG GTT GCT AGG CTG AGG ATA GAA AAT
1561 GTA ATA ATA ACA ACT TTG TAC AAA AAA TAA AAA AAA
1621 GTG AAA CAG CAC CAC AGG TTG        AA
```

RECOMBINANT HT$_{M4}$ GENE, PROTEIN AND ASSAYS

GOVERNMENT FUNDING

This invention was made with Government support under Grants DK44099 and CA42537 awarded by the National Institute of Health and Grant DE-FG02-86ER60408 from the Department of Energy. The Government has certain rights in the invention.

BACKGROUND OF THE INVENTION

Atopic diseases, which include allergy, asthma, atopic dermatititis (or eczema) and allergic rhinitis, together constitute one of the largest group of clinical disorders requiring medical intervention. In the United Kingdom alone, atopy gives rise to 3–5 million cases and as many as 2,000 deaths each year.

Atopy is generally defined as a disorder of Immunoglobulin E (IgE) responses to common antigens, such as pollen or house dust mites. It is frequently detected by either elevated total serum IgE levels, antigen specific IgE response or positive skin tests to common allergens. In principle atopy can result from dysregulation of any part of the pathway which begins with antigen exposure and IgE response to the interaction of IgE with its receptor on mast cells, the high affinity Fc receptor Fc$_\epsilon$RI, and the subsequent cellular activation mediated by that ligand-receptor engagement (Ravetch, *Nature Genetics*, 7:117–118 (1994). Cookson et al., *Lancet*, 333:1292–1295 (1989) have reported a genetic link between generalized atopic IgE responses and a locus on human chromosome 11q.

Fc$_\epsilon$RI, is part of a tetrameric receptor complex consisting of an α chain, a β chain and two γ chains (Kinet et al., *Proc. Natl. Acad. Sci. USA*, 15:6483–6487 (1988)). Together, they mediate interaction with IgE-bound antigens leading to dramatic cellular responses, such as the massive degranulations of mast cells. Thought until recently to be expressed only in mast cells and basophils, the high-affinity receptor Fc$_\epsilon$RI has been shown to be present also in Langerhans cells (Kinet, J.-P. et al., *Proc. Natl. Acad. Sci. USA* 85:6483–6487 (1988)), eosinophils (Sutton, B. J. and Gould, H. J., *Nature* (London) 366:421–428 (1993)) and peripheral monocytes (Gounni, A. S. et al., Ref 4). The β subunit, Fc$_\epsilon$RIβ, is a 4-transmembrane protein with both the amino and carboxyl termini residing in the cytoplasm. The human CD20 antigen (Tedder, T. F., et al., *Proc. Natl. Acad. Sci. USA* 85:208–212 (1988)), as well as its murine equivalent Ly-44 (Tedder, T. F. et al., *J. Immunol.* 141:4388–4394 (1988)), are expressed only in B-cells. Functional studies with different CD20 antibodies indicate that CD20 is involved in the regulation of B-cell activation (Clark, E. A. and Lane, J. L. *Annu. Rev. Immunol.* 9:97–127 (1991)). The CD20 protein also contain four transmembrane domains with the amino and carboxyl ends on the same cytoplasmic side of the cell membrane. There is an overall amino acid similarity of 16% between CD20 and Fc$_\epsilon$RIβ. Furthermore, the murine Fc$_\epsilon$RIβ gene maps to the same region in chromosome 19 as the Ly-44 gene (Huppi, K. et al., *J. Immunol.* 143:3787–3791 (1989)).

The identification of genes that may play a role in IgE responses or atopic diseases would be desirable. It would also be desirable to develop an assay which can detect hereditary atopy.

SUMMARY OF THE INVENTION

The invention relates to a recombinant DNA molecule which encodes a HT$_{m4}$ protein, a transfected host cell which has been stably transfected with a DNA molecule which encodes a HT$_{m4}$ protein and a recombinant HT$_{m4}$ protein. The invention also relates to a method for detecting the presence of a hereditary atopy.

BRIEF DESCRIPTION OF THE DRAWING

The FIGURE depicts the cDNA sequence of the HT$_{m4}$ gene and the amino acid sequence of the encoded protein. Nucleotide sequence is numbered on the left. The amino acid sequence of the longest open reading frame is numbered on the right beginning with the first presumed initiating methionine. An upstream in-frame stop codon, TAA, is indicated in bold letters at position 85. A TAA stop codon (END) is followed by a 3' untranslated region containing an AATAAA poly adenylation signal. The four putative transmembrane domains are underlined. Two phosphorylation sites are underlined with dotted lines.

DETAILED DESCRIPTION OF THE INVENTION

The invention relates to the discovery and cloning of the HT$_{m4}$ cDNA. The 1672-nucleotide long cDNA contains a long open reading frame, beginning at nucleotide position 97. The expression product of the cDNA is a 4 transmembrane spanning protein with a calculated molecular mass of about 25 kDa and 214 amino acids. The sequences are set forth in the FIGURE.

HT$_{m4}$ contains four hydrophobic domains of 20 to 21 amino acids. The amino terminal region before the beginning of the first hydrophobic domain contains four prolines. Each of the hydrophilic regions between the transmembrane segments contains a single proline. Several substrates for Casein kinase 2 phosphorylation (Pina, L. A. *Biochim. Biophys. Acta.* 1054:267–284 (1990)) of serine/threonine are found at residues 24 (TGPE), 155 (SSSE), 181 (TLLE), and 203 (SREE) and for Protein Kinase C phosphorylation at residue 149 (SLR). The sequence is consistent with a polypeptide chain that crosses the membrane four times, projecting two small loops extracellularly, and retaining the amino- and carboxyl-terminal portions in the cytoplasm.

The HT$_{m4}$ protein, as defined herein, encompasses an expression product which possesses one or more of the functions of the native protein. Included are functional protein or polypeptide fragments of the native protein and/or proteins or polypeptides where one or more amino acids have been deleted, added or substituted. Preferably, the protein or polypeptide shares at least about 50% homology and more preferably at least about 75% homology with the corresponding sequences of the native protein of the FIGURE.

Recombinant DNA molecules of the invention, in one embodiment, encode an HT$_{m4}$ protein, as defined herein. In one embodiment, the molecule shares at least about 50% homology, and preferably at least about 75% homology (such as at least about 90% homology) with the corresponding sequences of the native gene, particularly in highly conserved regions of the 4-transmembrane protein family of HT$_{m4}$, CD20 and Fc$_\epsilon$RIβ. Preferably, the recombinant DNA molecule comprises the corresponding encoding nucleotide sequences of the FIGURE.

In another embodiment recombinant DNA molecules, such as probes, can be employed, for example, to isolate genes encoding transmembrane proteins or receptors, such as the Fc$_\epsilon$RI. Such molecules comprise recombinant DNA molecules which hybridize to all of or a fragment of the sequences of the FIGURE. Preferably, the molecules hybridize under stringent conditions, such as those set forth in Sambrook et al. *Molecular Clonine: A Laboratory Manual,* 2nd Edition (Cold Spring Harbor Lab., Cold Spring Harbor, N.Y. (1989).

The recombinant DNA molecules can contain coding and non-coding sequences. Preferably, the molecules comprise at least about 25 nucleotides and more preferably at least about 60 nucleotides with 95–100% to pallout gene. Preferably, DNA probes comprise sequences the same as or homologous corresponding to the region encoding the N- or C-termini of the protein.

The predicted structure of $HT_{m4}$ as discussed herein demonstrates the relationship of this protein to $Fc_\epsilon RI\beta$ and the CD20 antigen and provides evidence for a family of 4-transmembrane spanning proteins. The conservation of amino acids between all three proteins is highest in the four transmembrane domains. While much greater divergence exist in the hydrophilic amino and carboxyl termini, several amino acids within these regions are conserved such as the presence of 4 to 5 prolines in the amino terminus of all three proteins. Two conserved cysteine residues in the second extracellular domain between Tm-3 and Tm-4 suggest that intra- or inter-molecular di-sulphide bonds in this domain are present in all three proteins. $HT_{m4}$ also contains two phosphorylation sites (threonine$^{24}$ and serine$^{203}$) in the cytoplasmic region of the protein. Finally, there is a well conserved SP(P) motif near the carboxyl end of all three proteins. The difference between CD20 and the other two proteins is contributed significantly by several long stretches of non-homologous amino acids. The carboxyl terminus of $Fc_\epsilon RI\beta$ contains the Reth or antigen receptor activation motif (ARAM) (Reth, M. *Nature* (London) 338:383–384 (1989)), which is not present in CD20 or $HT_{m4}$. The ARAM sequence is found in the cytoplasmic tail of several receptor subunits including CD3 $\gamma$, $\delta$, $\epsilon$ and $\zeta$, Ig$\alpha$ and Ig$\beta$, in MB-1 and B29 antigen, and in the $\beta$ and $\gamma$ chain of $Fc_\epsilon RI$ (Weiss, A. and Littman, D. R. *Cell* 76:263–274 (1994)). Tyrosine residues in ARAM sequences are believed to be critical inducers of and substrates for phosphorylation by cytoplasmic tyrosine kinases, allowing for the recruitment of additional effector molecules (Weiss, A. and Littman, D. R. *Cell* 76:263–274 (1994); Paolini, R. et al., *Nature* (London) 353:855–858 (1991); Eiseman, E. and Bolen, J. B. *Nature* (London) 355:78–80 (1992)). The common exon-intron organization of the genes containing the ARAM sequence has led to the suggestion that they might have evolved from the same gene family (Weiss, A. and Littman, D. R. *Cell* 76:263–274 (1994)). However, the structural similarity of $Fc_\epsilon RI\beta$ to CD20 and $HT_{m4}$ suggests that the ARAM sequence was acquired by the $Fc_\epsilon RI\beta$ gene during evolution.

Chromosome mapping localized the $HT_{m4}$ gene to chromosome 11q12-13.1, the location of the CD20 gene. However, the murine $Fc_\epsilon RI\beta$ and the murine equivalent for CD20, Ly-44, are both located in the same position in mouse chromosome 19 (Tedder, T. F. et al., *J. Immunol.* 141:4388–4394 (1988); Clark, E. A. and Lane, J. L. *Annu. Rev. Immunol.* 9:97–127 (1991); Huppi, K. et al., *J. Immunol.* 143:3787–3791 (1989)). Therefore, the three genes are believed to have been originated and evolved from the same locus, further supporting the proposition that they are members of the same family of related proteins. They also form a family of proteins that is quite distinct from another large family of 4-transmembrane proteins related to TAPA1 (Fearon, D. T. *Curr. Op. Immunol.* 5:341–348 (1993); Barclay, A. N. et al., *The Leucocyte Antigen Facts Book,* (Academic Press Inc., San Diego, Calif.) (1993)) which include CD9, CD37, CD532, CD63 and R2.

The identification of a gene product like $HT_{m4}$ related to $Fc_\epsilon RI\beta$ is significant. First, the exact importance of the $\beta$ subunit in $Fc_\epsilon RI$-expressing cells is currently not clear. While simultaneous cotransfection of the $\alpha$, $\beta$ and $\gamma$ genes are necessary to induce surface expression of the murine $Fc_\epsilon RI$ receptor, cotransfection of the human $\alpha$ and $\gamma$ genes without the $\beta$ gene is sufficient to induce expression of high-affinity Fc receptors (Miller, L. et al., *Science* 244:334–337 (1989)). Furthermore, recent evidence indicated that functional high-affinity IgE Fc receptors may be found on monocytes in the absence of the $\beta$ chain (Maurer, D. et al., *J. Exp. Med.* 179:745–750 (1994)).

As such, the $HT_{m4}$ gene and protein can be useful in the research and study of the induction of expression of $Fc_\epsilon RI$ and the particular function of $Fc_\epsilon RI\beta$. As such, the $HT_{m4}$ gene and protein can be useful in, for example, the design of drugs which can block or inhibit induction of $Fc_\epsilon RI$, thereby treating atopic diseases.

Further, the diverse association of subunits in Fc receptors of different hematopoietic cells has been established. For example, $Fc_\epsilon RI\beta$ was found to be associated with the low-affinity Fc receptor for IgG, Fc$\gamma$RIII (CD16), in mast cells (Kurosaki, T. et al., *J. Exp. Med.* 175:447–451 (1992)). $Fc_\lambda RI\gamma$ has also been found as a homodimer in association with F$\gamma$RIII in macrophages (Ra, C. et al., *Nature* 341:752–754 (1989)) or as a heterodimer with $\zeta$ and $\eta$ chains in T cell receptor complex (Orloff, D. G. et al., *Nature* 347:189 (1990)). In NK cells, $Fc_\epsilon RI\gamma$ may be found as homodimers and as a heterodimer with the $\zeta$-chain of T cell receptor (Letourneur, O. et al., *J. Immunol.* 147:2652–2656 (1991)). More recently others have shown that the $\gamma$ chain can also form an association with the high-affinity receptor for IgG, Fc$\gamma$RI (CD64), in monocytic cell lines and neutrophils (Scholl, P. R. and Geha, R. S. *Proc. Natl. Acad. Sci. USA* 90:8847–8850 (1993); Ernst, L. K., et al., *Proc. Natl. Acad. Sci. USA* 90:6023–6027 (1993)). These findings suggest that a variety of signal transduction complex composed of different subunits might mediate similar effector functions but with different functional consequences. Association of these subunits with alternative ligand recognition subunits in a multimeric receptor complex would allow coupling of distinct ligands to common signaling pathways.

The expression of $HT_{m4}$ in all hematopoietic lineages and not in any of the non-hematopoietic cells tested indicates that $HT_{m4}$ participates in biochemical pathways unique to hematopoietic lineages.

DNA probes comprising sequences of the $HT_{m4}$ genes can be used in an assay to detect patients suffering from hereditary atopic disorders. Also, the DNA sequences of the invention can be useful as probes to map genes on the human chromosome, such as employing the methods of fluorescence in situ hybridization (Kobayashi et al., *Blood,* 81:3027–3033 (1993)).

The $HT_{m4}$ protein can be employed in the preparation of antibodies, such as monoclonal antibodies, according to methods known in the art. The antibodies can be used to block or mimic ligand binding to the receptor comprising $HT_{m4}$ or other receptors, such as $Fc_\epsilon RI$, isolate the antibodies can be used to the $HT_{m4}$ protein or hematopoietic cells which contain the $HT_{m4}$ protein.

The antibodies can also be useful in the detection of hematopoietic cells in a sample. For example, the method comprises contacting the sample with the antibody under conditions sufficient for the antibody to bind to the $HT_{m4}$ protein and detecting the presence of bound antibody.

Exemplification

Materials and Methods

Cell Lines and Primary Cells

Hematopoietic cell lines used in this study included lymphomyeloid (DU528), erythroleukemic (K562,OCIR), promyelocytic (HL60), myeloblastic (KG-1), monoblastic (U937), T-cell leukemia/lymphoma (MOLT-4, Ly17, Ly13) and myeloma (OCI-My5) lines. Non-hematopoietic cell lines used included bone marrow stromal (BS-1), hepatoma (HepG2), melanoma (HS294), skeletal muscle (HuSk), neuroblastoma (SKNSH), cervical cancer (HeLa) and lung cancer (Calu-1) cells. All cell lines were maintained in Iscove's modified Dulbecco's medium supplemented with 10% fetal bovine serum and 1 mM L-glutamine, except for DU528, in which horse serum replaced bovine serum. Total RNAs from a human mast cell line, HMC-1 (Butterfield, J. H. et al., *Leuk. Res.* 12:345–355 (1988)), and a human factor dependent megakaryocytic line, MO7e, were kindly provided by Dr. Karl Nocka, Cytomed Inc., Cambridge, Mass. Normal bone-marrow cells were harvested from transfusion-filters after bone marrow transplantations. Primary leukemic cells with over 90% blasts were harvested from the peripheral blood of a patient with M4 acute myeloid leukemia. Total RNAs of neutrophils and eosinophils from normal individuals and eosinophils from a patient with hypereosinophilic syndrome were kindly provided by Dr. Peter Weller and Dr. Kaiser Lim, Harvard Medical School.

Preparation of Probes from Subtractive cDNA Libraries for Differential Screening The construction of four subtractive cDNA libraries (DU528/BS-1, K562/BS-1, KG-1/BS-1, and BS-1/BS-1), from three human hematopoietic cell lines (DU528, K562 and KG-1) and one non-hematopoietic human cell line (BS-1), using the PT3T719U multiphagemid vector (Pharmacia) was described previously (Lelias, J. M. et al., *Proc. Natl. Acad. Sci. USA* 90:1479–1483 (1993)). cDNA inserts released from two of the hematopoietic (DU528/BS-1 and KG-1/BS-1) and the non-hematopoietic (BS-1/BS-1) subtractive libraries were purified, labeled with $^{32}$p, and used as probes to screen the K562/BS-1 library (Sambrook, J. et al., *Molecular Cloning: A Laboratory Manual*, 2nd edition (Cold Spring Harbor Lab., Cold Spring Harbor, N.Y. (1989)).

Induction of Cell Line U937

The U937 cell line was grown to a concentration of 5×10$^5$ cells per ml and differentiation was induced with 50 nM phorbol 12-myristate 13-acetate (PMA; Sigma).

Chromosomal Localization of the HT$_{m4}$ Gene

The chromosomal location of the HT$_{m4}$ gene was determined by fluorescent in situ hybridization (FISH) as previously described (Kobayashi, H. et al., *Blood* 81:3027–3033 (1993)). Human metaphases were prepared from phytohemagglutinin-stimulated peripheral blood lymphocytes. The HT$_{m4}$ cDNA was labeled by nick-translation with biotin-11-UTP (Enzo Diagnostics, Syosset, N.Y.). The biotin-labeled probe was hybridized to metaphase cells and detected with fluorescein-conjugated avidin (Vector Lab, Burlingame, Calif.). Slides were examined by two independent observers without knowledge of the probe used.

Reverse-transcriptase Polymerase Chain Reaction (RT-PCR)

Reverse transcriptase reaction was carried out as described (Sanger, F. et al., *Proc. Natl. Acad. Sci. USA* 74:5463–5467 (1977)) with RNAs from cell lines or cells enriched for various cell types to obtain first strand cDNAs. The cDNAs were subjected to PCR amplification reactions as described (Wulf, G. M. et al., *EMBO J.* 12:5065–5074 (1993)), using primers spanning nucleotide 721 to 1087 of HT$_{m4}$ to give a predicted PCR product of 388 nucleotides. The sense primer used was 5'-TCACCTCCCAATTCTGT-GTAATCAAGA-3' (SEQ ID NO: 1), and the anti-sense primer was 5'-GATTATACCGCCTTCGTTCCTTAAACC-3' (SEQ ID NO: 2). PCR reactions were carried out with 100 nM primers for 30 cycles of denaturation (1 minute at 94° C.), annealing (1 minute at 54° C.) and extension (2 minutes at 72° C.).

General Methods

RNA was isolated using the RNAzol method (Biotecx Laboratories, Houston, Tex.). DNA sequencing was done by the dideoxynucleo-tide chain-termination technique (Sanger, F. et al., *Proc. Natl. Acad. Sci. USA* 74: 5463–5467 (1977)) after subcloning appropriate DNA fragments into M13.

Results

Isolation of Clone HT$_{m4}$

By differential screening of the K562 hematopoietic library with cDNA probes from two hematopoietic libraries (enriched for hematopoietic cDNAs) and cDNA probes from the non-hematopoietic BS-1 library, clones that hybridized positively only to the hematopoietic probes were isolated. One of these, denoted clone HT$_{m4}$ was used as a probe to screen a Northern blot panel consisting of total RNAs from various hematopoietic and non-hematopoietic cell lines.

Expression pattern of HT$_{m4}$

A combination of Northern blot and RT-PCR analysis was used to determine the spectrum of tissue and lineage expression of the gene. The cDNA insert of clone HT$_{m4}$ hybridized to a transcript of about 1.7 kb in five hematopoietic lines which included myeloid and erythroid lineages and to normal human bone marrow cells. The HT$_{m4}$ and mRNA was not detectable in a T cell lymphoma line (Ly17) and in a lymphomyeloid leukemic line with T and granulocytic differentiation potential (DU528). In all of the seven non-hematopoietic cell lines which included lung, cervical, brain, skeletal muscle, melanoma, hepatoma, and bone marrow stromal cells, no hybridizing mRNA could be detected. These non-hematopoietic lines included cells of ectodermal, endodermal and mesodermal origin. The mRNA was also absent in the primary blast cells of a patient diagnosed to have M4 acute myeloid leukemia (AML).

To facilitate screening of RNA samples, particularly those derived from cells in quantities too limited for Northern blot analysis, we examined expression by RT-PCR. The quality of the first strand cDNAs obtained after reverse transcription was satisfactory as evaluated by using primers for the housekeeping gene HPRT. Based on nucleotide sequence of HT$_{m4}$ cDNA, oligonucleotides were synthesized and used as specific primers for PCR amplification. The predicted PCR product of a 388 nucleotide-long DNA was obtained in normal bone marrow cells and the HL60 cell line but not in the HeLa and Ly17 cell line, confirming the Northern blot analysis. RNAs from a human mast cell line (HMC-1) and a megakaryocytic line (MO7e) were also positive for $HT_{m4}$ mRNA. RNAs from normal eosinophils or neutrophils and eosinophils from a patient with hyper-eosinophilic syndrome (HES) also yielded the predicted PCR product. Two leukemic T-cell lines (Ly13 and MOLT4) and a myeloma cell line (OCI-My5) were also found to be positive for $HT_{m4}$. All PCR-derived DNAs hybridized positively to radio-labeled $HT_{m4}$ in subsequent Southern analysis.

Molecular analysis of $HT_{m4}$ human cDNA

The nucleotide sequence of the $HT_{m4}$ cDNA and the predicted amino acid sequence are shown in the FIGURE. The 1672-nucleotide long cDNA contains a long open reading frame, beginning at nucleotide position 97, encoding a protein of 214 amino acids with a calculated molecular mass of 25 kDa. A hydrophilicity analysis with the Kyte-Doolittle algorithm (Kyte, J. and Doolittle, R. F. *J. Mol. Biol.* 157:105–132 (1982)), reveals that $HT_{m4}$ contains four hydrophobic domains of 20 to 21 amino acids. The amino terminal region before the beginning of the first hydrophobic domain contains four prolines. Each of the hydrophilic regions between the transmembrane segments contains a single proline. Several substrates for Casein kinase 2 phosphorylation (Pina, L. a. *Biochim. Biophys. Acta* 1054:267–284 (1990)) of serine/threonine are found at residues 24 (TGPE), 155 (SSSE), 181 (TLLE), and 203 (SREE) and for Protein Kinase C phosphorylation at residue 149 (SLR). The sequence is consistent with a polypeptide chain that crosses the membrane four times, projecting two small loops extracellularly, and retaining the amino- and carboxyl-terminal portions in the cytoplasm.

Expression of $HT_{m4}$ during differentiation of cell line U937

To ascertain if expression of the $HT_{m4}$ mRNA may vary depending on the stage of cellular differentiation, we examined the consequences of induced differentiation in the monoblastic cell line U937. Exposure of the cells to PMA rapidly induced differentiation to macrophages, as confirmed morphologically and molecularly by monitoring the marker for terminally differentiated macrophages, CD11b (Arnout, M. A. *Immunol. Rev.* 114:145–180 (1990)). The expression of $HT_{m4}$ mRNA over a period of 48 hours showed an initial increase followed by a down regulation so that by day three, $HT_{m4}$ transcripts were detectable at a very low level.

$HT_{m4}$ is located on chromosome 11q12-13

Forty-one chromosomes from 30 metaphases were scored for the positive chromosomal band. Band 11q12 was labeled on eighteen of chromosome 11 homologues, band 11q13.1 on twenty-one of chromosome 11 homologues and band 11q13.2 on two of chromosome 11 homologues. No signal was detected on other chromosomes in these cells. Similar results were obtained in an additional experiment using this probe. Thus, $HT_{m4}$ is localized to chromosome 11q12-q13.1.

Equivalents

Those skilled in the art will know, or be able to ascertain, using no more than routine experimentation, many equivalents to the specific embodiments of the invention described herein. These and all other equivalents are intended to be encompassed by the following claims.

What is claimed is:

1. A recombinant DNA molecule which encodes a mammalian $HT_{m4}$ protein.

2. The DNA molecule of claim 1 characterized by the nucleotide sequence of SEQ. ID NO: 3.

3. A DNA vector comprising the sequence of SEQ. ID NO.:3.

4. A transfected host cell which has been stably transfected with a recombinant DNA molecule according to claim 1.

5. A transfected host cell which has been stably transfected with a recombinant DNA molecule according to claim 3.

6. The DNA molecule of claim 1 which encodes a human $HT_{m4}$ protein.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

TCACCTCCCA ATTCTGTGTA ATCAAGA 27

( 2 ) INFORMATION FOR SEQ ID NO:2:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

GATTATACCG CCTTCGTTCC TTAAACC 27

( 2 ) INFORMATION FOR SEQ ID NO:3:

( i ) SEQUENCE CHARACTERISTICS:
        ( A ) LENGTH: 1661 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 97..741

( x i ) SEQUENCE DESCRIPTION: SEQ ID NO:3:

```
GTGATCTTTT CTGAGTGTCT CCTACTTGCG ACAAGGTGGA CTTGGGAGGA AAGCCGTCTG        60

CCAAAGCCTG AAGCCTCCAA GCCATAAACA ACCCCA ATG GCC TCC CAC GAA GTT        114
                                        Met Ala Ser His Glu Val
                                        1               5

GAT AAT GCA GAG CTG GGG TCA GCC TCT GCC CAT GGT ACC CCA GGC AGT        162
Asp Asn Ala Glu Leu Gly Ser Ala Ser Ala His Gly Thr Pro Gly Ser
            10                  15                  20

GAG ACG GGA CCA GAA GAG CTG AAT ACT TCT GTC TAC CAC CCC ATA AAT        210
Glu Thr Gly Pro Glu Glu Leu Asn Thr Ser Val Tyr His Pro Ile Asn
        25                  30                  35

GGA TCA CCA GAT TAT CAG AAA GCA AAA TTA CAA GTT CTT GGG GCC ATC        258
Gly Ser Pro Asp Tyr Gln Lys Ala Lys Leu Gln Val Leu Gly Ala Ile
    40                  45                  50

CAG ATC CTG AAT GCA GCA ATG ATT CTG GCT TTG GGT GTC TTT CTG GGT        306
Gln Ile Leu Asn Ala Ala Met Ile Leu Ala Leu Gly Val Phe Leu Gly
55                  60                  65                  70

TCC TTG CAA TAC CCA TAC CAC TTC CAA AAG CAC TTC TTT TTC TTC ACC        354
Ser Leu Gln Tyr Pro Tyr His Phe Gln Lys His Phe Phe Phe Phe Thr
                75                  80                  85

TTC TAC ACA GGC TAC CCG ATT TGG GGT GCT GTG TTT TTC TGT AGT TCA        402
Phe Tyr Thr Gly Tyr Pro Ile Trp Gly Ala Val Phe Phe Cys Ser Ser
            90                  95                  100

GGA ACC TTG TCT GTT GTA GCA GGG ATA AAA CCC ACA AGA ACA TGG ATA        450
Gly Thr Leu Ser Val Val Ala Gly Ile Lys Pro Thr Arg Thr Trp Ile
        105                 110                 115

CAG AAC AGT TTT GGA ATG AAC ATT GCC AGT GCT ACA ATT GCA CTA GTG        498
Gln Asn Ser Phe Gly Met Asn Ile Ala Ser Ala Thr Ile Ala Leu Val
    120                 125                 130

GGG ACT GCT TTT CTC TCA CTA AAT ATA GCA GTT AAT ATC CAG TCA TTA        546
Gly Thr Ala Phe Leu Ser Leu Asn Ile Ala Val Asn Ile Gln Ser Leu
135                 140                 145                 150

AGG AGT TGT CAC TCT TCA TCA GAG TCA CCG GAC CTA TGC AAT TAC ATG        594
Arg Ser Cys His Ser Ser Ser Glu Ser Pro Asp Leu Cys Asn Tyr Met
                155                 160                 165

GGC TCC ATA TCA AAT GGC ATG GTG TCT CTA CTG CTG ATT CTC ACC TTG        642
Gly Ser Ile Ser Asn Gly Met Val Ser Leu Leu Leu Ile Leu Thr Leu
            170                 175                 180

CTG GAA TTA TGC GTA ACT ATC TCT ACC ATA GCC ATG TGG TGC AAT GCA        690
Leu Glu Leu Cys Val Thr Ile Ser Thr Ile Ala Met Trp Cys Asn Ala
        185                 190                 195

AAC TGC TGT AAT TCA AGA GAG GAA ATT TCC TCA CCT CCC AAT TCT GTG        738
Asn Cys Cys Asn Ser Arg Glu Glu Ile Ser Ser Pro Pro Asn Ser Val
    200                 205                 210

TAATCAAGAA TACCTCCTTA TGAAATAAT TCTGAGAGCA TGAATATTTG ACCTTAAATC        798

TCCAGTGACT CAGAGCTTCA CCCACAAACT CAGGAGAACA TAAGCCTGCT CGTAAAGCTC       858

AATCCTTCTA TCATGGCACC AATCACAAGA ACCTTGGACG TTTGACTGAC TCTATCCTTT       918
```

-continued

| | | | | | |
|---|---|---|---|---|---|
| CTCTCCTAAC | TATAAATCCT | ATTTGTGTGT | CGTGGGTATG | GAAGGACAGA | TATATTTCTT | 978 |
| TAGGCATTCT | TGGATATCTG | TAACTTCTAT | GATCATTACT | CCAAAGTTGT | TTCCAGAAAT | 1038 |
| TGGTTCTATT | TCTTCTTATC | CACCTACTCC | ATTGCTTTAT | GAGGTTTAAG | GAAGGAAGGC | 1098 |
| GGTATAATCC | CTATTCAATA | TATTTTTTCT | AAAATCCAAC | TTCTGACCGC | CCAGTAGGAA | 1158 |
| GAAAAATGAG | ACATTTTTC | CATTACAGAG | AAATGCTTCT | TGACTTTAAC | ATCAGCATTA | 1218 |
| TAAAAGTGT | CAAATAAAAA | ATTACCATCA | TTATCATTAA | AATAAATTTT | CACTGTATTT | 1278 |
| GAGATGGGAG | GGTTAAGGCT | CAGGGATTTT | ATTTCAGTGA | ACTGCTGGAA | CTCACACATG | 1338 |
| CCCTGATATG | TAAATGATGA | TTTATGTTGG | CGAGTCTGAG | AGCAAGCCCA | AATGTGTTCT | 1398 |
| TCAAAGGACA | ATGGGAAACT | GTAAAGTAGA | GAACTAAAGA | ATAAGGCCTT | TAGAATCTGA | 1458 |
| CACATCTGGG | TTCAAATTCT | GAAACTGTCA | CTTATTACCT | GTATGAACAT | GGGCAAATTA | 1518 |
| TCTAATCTCT | CTGATCTATT | TTTCCTCATC | TGTAAAATAG | GTGTAATAAT | AACAACTACT | 1578 |
| TTGTCGGTTG | CTCTGAGGGT | TAAATGAAAA | TAAAAGAAA | ATGTGAAACA | GCACCACAGG | 1638 |
| TACTTGAAAA | AAAAAAAAAA | AAA | | | | 1661 |

( 2 ) INFORMATION FOR SEQ ID NO:4:

( i ) SEQUENCE CHARACTERISTICS:
        ( A ) LENGTH: 214 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Met Ala Ser His Glu Val Asp Asn Ala Glu Leu Gly Ser Ala Ser Ala
 1               5                  10                  15

His Gly Thr Pro Gly Ser Glu Thr Gly Pro Glu Glu Leu Asn Thr Ser
            20                  25                  30

Val Tyr His Pro Ile Asn Gly Ser Pro Asp Tyr Gln Lys Ala Lys Leu
        35                  40                  45

Gln Val Leu Gly Ala Ile Gln Ile Leu Asn Ala Ala Met Ile Leu Ala
    50                  55                  60

Leu Gly Val Phe Leu Gly Ser Leu Gln Tyr Pro Tyr His Phe Gln Lys
65                  70                  75                  80

His Phe Phe Phe Phe Thr Phe Tyr Thr Gly Tyr Pro Ile Trp Gly Ala
                85                  90                  95

Val Phe Phe Cys Ser Ser Gly Thr Leu Ser Val Val Ala Gly Ile Lys
            100                 105                 110

Pro Thr Arg Thr Trp Ile Gln Asn Ser Phe Gly Met Asn Ile Ala Ser
        115                 120                 125

Ala Thr Ile Ala Leu Val Gly Thr Ala Phe Leu Ser Leu Asn Ile Ala
    130                 135                 140

Val Asn Ile Gln Ser Leu Arg Ser Cys His Ser Ser Glu Ser Pro
145                 150                 155                 160

Asp Leu Cys Asn Tyr Met Gly Ser Ile Ser Asn Gly Met Val Ser Leu
                165                 170                 175

Leu Leu Ile Leu Thr Leu Leu Glu Leu Cys Val Thr Ile Ser Thr Ile
            180                 185                 190

Ala Met Trp Cys Asn Ala Asn Cys Cys Asn Ser Arg Glu Glu Ile Ser
        195                 200                 205

Ser Pro Pro Asn Ser Val
    210
```